Feb. 5, 1974 W. C. BIRTWELL Re. 27,910

CATHETER

Original Filed Feb. 15, 1968

INVENTOR.
William C. Birtwell
BY
Wolf, Greenfield & Hiken
ATTORNEYS

United States Patent Office

Re. 27,910
Reissued Feb. 5, 1974

27,910
CATHETER

William C. Birtwell, North Scituate, R.I., assignor to Biomedical Engineering Associates, Inc., Boston, Mass.

Original No. 3,547,126, dated Dec. 15, 1970, Ser. No. 705,667, Feb. 15, 1968. Application for reissue July 29, 1971, Ser. No. 167,535
Int. Cl. A61m *25/00*
U.S. Cl. 128—349 B 8 Claims

Matter enclosed in heavy brackets [ ] appears in the original patent but forms no part of this reissue specification; matter printed in italics indicates the additions made by reissue.

ABSTRACT OF THE DISCLOSURE

A Foley-type balloon catheter having an extruded body made of silicone rubber with a single drainage lumen and a plurality of inflation lumens, and a molded tip of silicone rubber attached to the body and having a drainage eye communicating with the drainage lumen, and a molded funnel attached to the other end of the body and having passages which communicate with drainage and inflation lumens.

Figure 1:
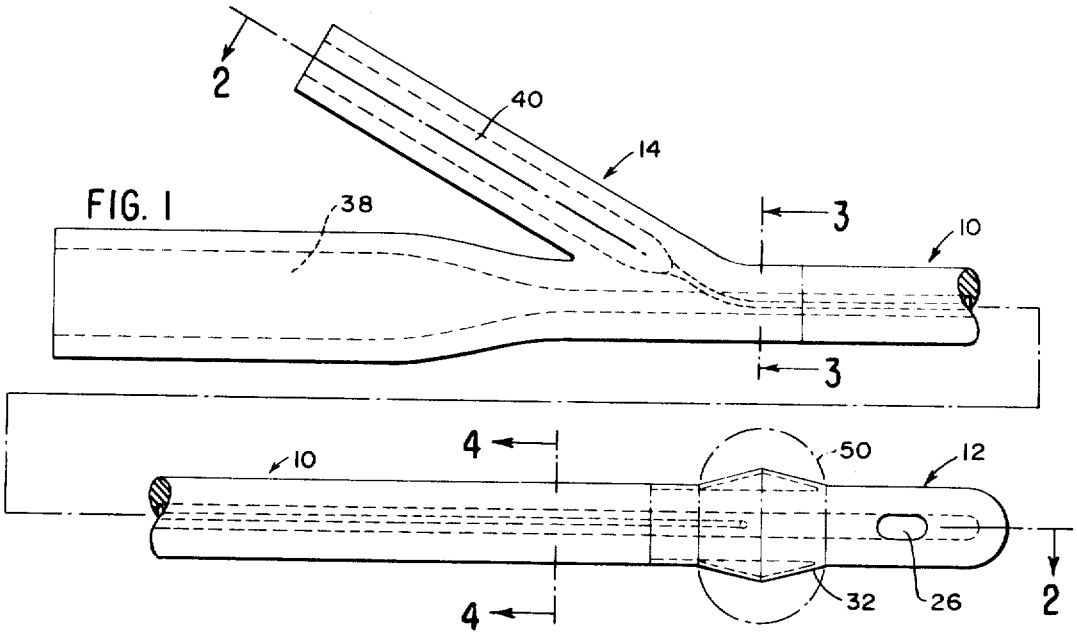

This invention relates to catheters and more particularly comprises a new and improved urethral drainage catheter used as an in-dwelling drainage catheter for the bladder.

At the present time the Foley balloon catheter is universally used as a drainage catheter for the bladder. It is used in cases of incontinence and also to form a drainage outlet when for any reason the patient cannot release urine from the bladder because of a constriction in the urethra. The catheter is introduced into the bladder via the urethra which in the male is a relatively tortuous tube of varying cross-sectional dimensions and is normally collapsed along most of its length. The upper portion of the urethra is provided with sphincters or valves where it enters the bladder neck. In the female the urethra is shorter and straighter but otherwise functionally the same.

From the standpoint of the urethra and sphincter [and] *the* catheter should be smooth, round, and as small as possible consistent with its drainage function. The tip should be smooth and rounded so that it may be introduced through the passage with a minimum of pain and discomfort. The drainage eyes provided in the catheter tip should have no sharp edges, and they should be shaped to provide a smooth outlet for urine. The catheter tube should bend easily to the longitudinal path of the urethra but it should have good cross-sectional stability to prevent kinking and collapse in the areas of the urethra which may be constricted.

The tip of the catheter is disposed within the bladder which is a dome-shaped container with muscular walls and which accepts urine from the kidneys. The urine is stored in the bladder until voluntarily released by simultaneous muscular contraction of the walls and opening of the sphincter. Under normal circumstances, the bladder is continually filling from the kidneys, and from time to time it is emptied voluntarily. When the catheter is introduced, the bladder is continually drained and thus is as empty as the location of the drainage holes or eyes in the catheter tip permit. Therefore, from the standpoint of the bladder, the tip of the catheter should be smooth and atraumatic to minimize the irritation caused by the empty bladder wall resting on the tip. The drainage eyes should be as low in the bladder as possible to minimize the residual volume in the bladder.

The Foley catheter includes a balloon at the tip which is inflated after the catheter is introduced in the urethra with the tip lying in the bladder. The balloon is inflated in the bladder and serves as an anchor to retain the catheter in place. The balloon must be deflated before the catheter may be withdrawn, and it should be as smooth and as soft as is consistent with its retention function so as not to irritate the bladder. The balloon should merge into the body and tip of the catheter smoothly and present no shoulders particularly at its leading edge.

Still other considerations dictate the physical characteristics of the catheter. For example, the inside lumen of the catheter used as the urine drain should be as large as possible to prevent clogging of the catheter by clots or debris from a diseased bladder. Therefore, the wall of the tube should be as thin as practical so as to minimize the outside diameter. This consideration is somewhat in conflict with the requirement of cross-sectional stability, and therefore these considerations must be resolved to satisfy each requirement.

Although the balloon catheter has proved to be a practical and essential device for controlling problems related to the drainage of the bladder, there are several unfortunate consequences often related to its use. These include (1) infection caused by the use of a catheter; (2) damage to the sphincter caused during entry or exit of the catheter; (3) pain and discomfort related to the introduction, presence, and withdrawal of the catheter; and (4) hazard of defective balloon function usually caused when the balloon cannot be deflated for withdrawal.

Substantially all balloon catheters which have been used to this time have been made of latex rubber by the dipping process. However, latex rubber is wettable and somewhat irritating, and it reacts with the urine. Its physical characteristics such as tensile strength and resilience are reduced when it is wet. The main advantage of the dipping technique used in its production is the one-piece product that is achieved with the balloon smoothly and permanently incorporated into the wall of the catheter. However, there are many disadvantages which effect the uniformity and quality of a catheter manufactured by the dipping technique. The disadvantages are (1) the catheter is seldom round in cross section and varies in diameter along its length because of variable runoff; (2) the tips are not uniform for the same reasons; (3) the drainage eyes are usually cut and burned, and they are not uniform and do not have rounded edges; (4) the wall of the drainage lumen inside the balloon is thinner than it is along the fully built-up portions of the catheter; (5) the wall is variable in thickness as a result of process variations; (6) the longitudinal tension produced in the wall of the drainage lumen as the balloon is inflated, stretches it and tends to collapse the lumen; (7) when the latex rubber is wet by the inflation medium, the drainage wall weakens and aggravates the tendency of the wall to stretch and collapse; (8) atmospheric conditions, production cycling, and material often cause poor adhesion betwen adjacent plys of the catheter which is built up of several layers. Many defects in the catheter can be traced to the failure of the bonds between the layers. The most serious problem is the slow deflating or nondeflating balloons which are directly traceable to the separation and collapse of the first thin layer on the inflation lumen.

One important object of this invention is to provide a urethral drainage balloon catheter having a uniform hemispherical shaped tip.

Another important object of this invention is to provide a drainage catheter having uniform drainage eyes with smooth rounded edges.

Still another important object of this invention is to eliminate any shoulders or other protrusions at the leading edge of the catheter, which would interfere with its introduction through the urethra.

And another important object of this invention is to provide a urethral drainage catheter composed of a single layer of material.

Another important object of this invention is to provide a catheter made of material which is physiologically acceptable.

Yet another important object of this invention is to provide a plurality of inflation lumens in the wall of the tube so as to provide greater assurance of balloon deflation.

To accomplish these and other objects, the drainage catheter of this invention is basically formed in three parts, namely, a tip, a body or tube, and a funnel. The three parts are made of a silicone rubber, with the tip and funnel being molded and the tube being extruded of the material. Two inflation lumens in addition to the drainage lumen are formed in the extruded tube, and the inflation lumens communicate with a balloon defined by a flap formed as an integral part of the tip and secured to the body.

Figure 2:
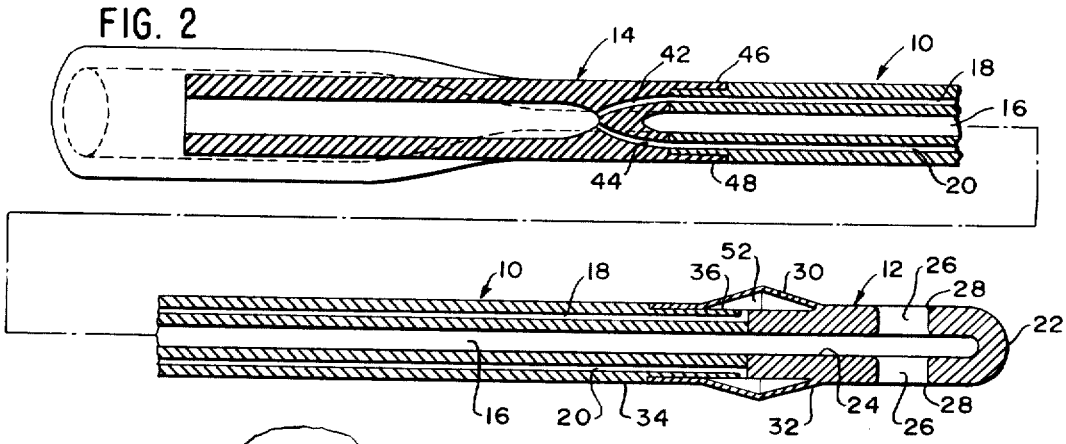
Figure 3:
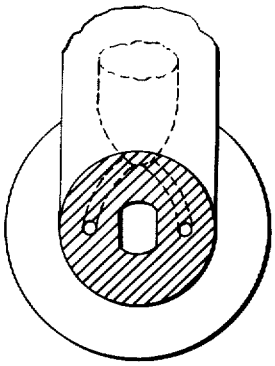
Figure 4:
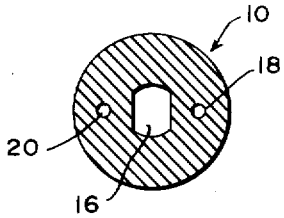

These and other objects and features of this invention along with its incident advantages will be better understood and appreciated from the following detailed description of one embodiment thereof, selected for purposes of illustration and shown in the accompanying drawing, in which:

FIG. 1 is a side view of a drainage catheter constructed in accordance with this invention; and FIGS. 2–4 are cross-sectional views taken along the corresponding section lines in FIG. 1.

The drainage catheter shown in the drawing is composed of a main body in the form of a tube 10, a tip 12, and a funnel 14. The three parts are made of silicone rubber which has the necessary physiological acceptability, physical characteristics, and productability. To satisfy the physiological requirements, the material should be nonwetting, inert, smooth, soft, flexible and stretchable as well as nontoxic and nonreactive. The silicone rubber has the physical characteristics which are necessary to facilitate the function of the device, and the material obviously lends itself to mass production techniques.

The body 10 is formed as an extruded tube having a uniform outside diameter with no taper. As an extruded tube, it is a single layer of material and cannot delaminate. The extruded tubular body 10 includes a central drainage lumen 16 and a pair of inflation lumens 18 and 20 which extend longitudinally throughout the entire length of the tube. The size of the drainage lumen 16 is as large as possible as compared to the outer diameter of the tube without sacrificing cross-sectional stability necessary to avoid kinking and collapse of the tube. The cross-sectional configuration of the drainage lumen 16 is a generally circular with flattened sides to provide adequate cross section for the two inflation lumens 18 and 20.

The tip 12 molded of silicone rubber is provided with a uniform hemispherical leading edge 22 and a central drainage passage 24 which communicates with the drainage lumen 16 in the tube 10. The drainage passage 24 in the tip communicates with a pair of oppositely disposed drainage eyes 26 of which has smooth rounded exterior edges 28 to reduce the irritation and discomfort incident to the insertion of the catheter into and through the urethra. A thin, soft and stretchable balloon flap 30 is molded as an integral part of the tip 12, and as shown in FIGS. 1 and 2 that the leading edge 32 of the balloon is free of any sharp protuberances or shoulders which would impair the insertion of the balloon portion of the tip into and through the urethra. The flap 30 extends rearwardly over the outer surface 34 of the tube 10, and an undercut or seat 36 is provided in the outer surface 34 to receive the rear or trailing portion of the flap. It is evident in FIGS. 1 and 2 that this particular construction which could interfere with the insertion or withdrawal avoids the formation of any shoulder or other obstruction of the catheter. Rather, the surface of the trailing edge of the balloon flap 30 is a smooth continuation of the outer surface 34 of the tube. The ends of the inflation lumens 18 and 20 turn radially outward as shown in FIG. 2 and terminate within the annular chamber defined by the flap 30.

The funnel 14 also molded of silicone rubber includes a drainage passage 38 and an inflation passage 40 which at its forward end divides into a pair of passages 42 and 44 that communicate with the inflation lumens 18 and 20 in the tube when the funnel is assembled on the tube. The funnel also includes a flap 46 which extends over an undercut portion 48 provided in the tube similar to the seat 36 at the front end of the tube which receives balloon flap 30.

To assemble the funnel and tip on the tube, final curing of the parts takes place only after the three parts are united to assure good adhesion. Each of the parts is semicured before assembling, and after assembling with a suitable solvent, the parts are finally cured for maximum adhesion strength.

From the foregoing description it will be appreciated that the several objects set forth in the introduction are achieved by the embodiment of this invention described. Moreover, the limitations found in the universally employed Foley catheter now available have been eliminated. The particular material from which the catheter of this invention is made satisfies all of the requirements outlined. It is evident that the embodiment shown and described is eminently suitable for its intended purposes. The silicone rubber has the necessary physical characteristics to make it a satisfactory substitute for latex rubber and may be extruded to eliminate the long and costly procedure of dipping to form the device. Its flexibility allows the balloon formed by the flap 30 to inflate to the size suggested by the broken lines 50 in FIG. 1 to form a suitable anchor for the catheter. The chamber 52 of the balloon may be completely drained through each of the inflation lumens 18 and 20 provided in the body, and failure of one inflation lumen will not produce the hazardous situation which results when the single inflation lumen now universally used becomes defective in the Foley catheters.

Because numerous modifications may be made of this invention without departing from its spirit, it is not intended to limit the breadth of this invention to the single embodiment illustrated and described. Rather, it is intended that the scope of this invention be determined by the appended claims and their equivalents.

I claim:

1. A urethral drainage catheter comprising:

[top] *a tip* portion *of one-piece construction and* having forward and rearward ends and a drainage lumen extending longitudinally therein, said tip portion also having therein a drainage eye adjacent the forward end, [a drainage eye] *and* communicating with the drainage lumen, *said tip portion further including an annular balloon flap;* an elongated body being circular in cross section with an annular wall and connected to the rearward end of the tip; *said* [an] annular balloon flap [formed integrally] *being of one-piece construction with and integral* with said tip and connected and extending, from a point intermediate the ends of said tip portion rearwardly beyond the rear portion and rear end of said tip, the trailing end of the flap being secured to the external surface of the elongated body, said flap forming an annular inflatable chamber about the portion of the tip rearwardly of [said] *the* point of connection between said tip portion and said flap;

a drainage lumen in the body aligned with and forming a continuation of the drainage lumen in the tip;

at least one inflation lumen extending through the body and formed in its annular wall and communicating with the inflatable chamber for inflating and deflating the inflatable chamber; and means attached to the other end of the body and having passages which communicate with the drainage and inflation lumens.

2. A urethral drainage catheter as defined in claim 1 further characterized by said body and tip being made of silicone rubber.

3. A urethral drainage catheter as defined in claim 1 further characterized by the body at the end attached to the tip being of reduced diameter and receiving the flap of the tip to eliminate the formation of a shoulder where the tip is attached to the body.

4. A urethral drainage catheter as defined in claim 2 further characterized by the body at the end attached to the tip being of reduced diameter and receiving the flap of the tip to eliminate the formation of a shoulder where the tip is attached to the body.

5. A urtethral drainage catheter as defined in claim 4 further characterized by said body having two inflation lumens symmetrically arranged in the wall about the drainage lumen.

*6. A urethral drainage catheter comprising:*

*a tip portion of one-piece construction and having forward and rearward ends and a drainage lumen extending longitudinally therein, said tip portion also having therein a drainage eye adjacent the forward end and communicating with the drainage lumen said tip portion further including an annular balloon flap;*

*an elongated body being circular in cross-section with an annular wall and connected to the rearward end of the tip;*

*said annular balloon flap being of one-piece construction with and integral with said tip and extending rearwardly from said tip beyond the point of connection of said tip and said elongated body, the trailing end of the flap being secured to the external surface of the elongated body, said flap forming an annular inflatable chamber, rearwardly of the point of connection between said tip portion and said flap;*

*a drainage lumen in the body aligned with and forming a continuation of the drainage lumen in the tip;*

*at least one inflation lumen extending through the body and formed in its annular wall and communicating with the inflatable chamber for inflating and deflating the inflatable chamber; and*

*means atached to the other end of the body and having passages which communicate with the drainage and inflation lumens.*

*7. A urethral drainage catheter comprising:*

*a tip portion of one-piece construction and having forward and rearward ends and a drainage lumen extending longitudinally therein, said tip also having therein a drainage eye adjacent the forward end and communicating with the drainage lumen said tip portion further including an annular balloon flap;*

*an elongated body being circular in cross-section with an annular wall and connected to the rearward end of the tip;*

*said annular balloon flap being of one-piece construction with and integral with said tip and extending rearwardly therefrom beyond the rear end of said tip portion, the trailing end of the flap being secured to the external surface of the elongated body, said flap defining an annular inflatable chamber at least about a portion of said elongated body, said chamber being disposed rearwardly of the point of connection between said tip portion and said flap;*

*a drainage lumen in the body aligned with and forming a continuation of the drainage lumen in the tip;*

*at least one inflation lumen extending through the body and formed in its annular wall and communicating with the inflatable chamber for inflating and deflating the inflatable chamber; and*

*means attached to the other end of the body and having passages which communicate with the drainage and inflation lumens.*

*8. A urethral drainage catheter comprising:*

*a tip portion of one-piece construction and having forward and rearward ends and a drainage lumen extending longitudinally therein, said tip portion also having therein a drainage eye adjacent the forward end and communicating with the drainage lumen said tip portion further including an annular balloon flap;*

*an elongated body having a forward end and a rearward end, said body being circular in cross-section with an annular wall and abuttingly connected to the rearward end of the tip;*

*said annular balloon flap being of one-piece construction with and integral with said tip and connected thereto at a point no further rearward than the point of connection between said tip and said elongated body, said flap extending rearwardly from said tip beyond the juncture of said tip and said elongated body, the trailing end of the flap being secured to the external surface of the elongated body, said flap forming an annular inflatable chamber in cooperation with at least the forward end of said elongated body;*

*a drainage lumen in the body aligned with and forming a continuation of the drainage lumen in the tip;*

*at least one inflation lumen extending through the body and formed in its annular wall and communicating with the inflatable chamber for inflating and deflating the inflatable chamber; and*

*means attached to the other end of the body and having passages which communicate with the drainage and inflation lumens.*

References Cited

The following references, cited by the Examiner, are of record in the patented file of this patent or the original patent.

UNITED STATES PATENTS

| | | | |
|---|---|---|---|
| 2,701,559 | 2/1955 | Cooper | 128—2 |
| 2,912,981 | 11/1959 | Keough | 128—349 B |
| 2,936,761 | 5/1960 | Snyder | 128—349 B |
| 3,112,748 | 12/1963 | Colburn | 128—350 R |
| 3,292,627 | 12/1966 | Harautuneian | 128—349 R |
| 2,610,626 | 9/1952 | Edwards | 128—231 |

FOREIGN PATENTS

| | | | |
|---|---|---|---|
| 674,134 | 6/1952 | Great Britain | 128—349 |
| 819,225 | 9/1959 | Great Britain | 128—349 |

DALTON L. TRULUCK, Primary Examiner